(12) United States Patent
Parison

(10) Patent No.: US 7,401,520 B2
(45) Date of Patent: Jul. 22, 2008

(54) VEHICLE TESTING APPARATUS FOR APPLYING VERTICAL FORCE TO A WHEEL

(75) Inventor: James A. Parison, New Ipswich, NH (US)

(73) Assignee: Bose Corporation, Framingham, MA (US)

( * ) Notice: Subject to any disclaimer, the term of this patent is extended or adjusted under 35 U.S.C. 154(b) by 19 days.

(21) Appl. No.: 11/464,156

(22) Filed: Aug. 11, 2006

(65) Prior Publication Data

US 2007/0044546 A1 Mar. 1, 2007

Related U.S. Application Data

(60) Provisional application No. 60/711,882, filed on Aug. 26, 2005.

(51) Int. Cl.
*G01M 17/00* (2006.01)
(52) U.S. Cl. ....................................................... 73/669
(58) Field of Classification Search ................ 73/118.1, 73/669, 670, 112, 116, 117, 117.1, 117.2, 73/117.3, 121, 122, 123, 124, 125, 126
See application file for complete search history.

(56) References Cited

U.S. PATENT DOCUMENTS

| | | | |
|---|---|---|---|
| 3,720,091 A | 3/1973 | Kiefer | |
| 3,815,404 A | 6/1974 | Brisard | |
| 3,827,289 A * | 8/1974 | Borg | 73/669 |
| 4,455,866 A | 6/1984 | Barriger | |
| 4,689,998 A * | 9/1987 | Jackson et al. | 73/669 |
| 4,768,374 A * | 9/1988 | Fouchey | 73/118.1 |
| 5,048,342 A * | 9/1991 | Morelli | 73/669 |
| 5,394,731 A | 3/1995 | Shechet et al. | |
| 5,487,301 A | 1/1996 | Müller et al. | |
| 5,610,330 A | 3/1997 | Fricke et al. | |
| 5,750,890 A | 5/1998 | Fricke et al. | |
| 5,756,877 A | 5/1998 | Nozaki | |
| 5,767,382 A | 6/1998 | Buchanan | |
| 5,942,673 A | 8/1999 | Horiuchi et al. | |
| 6,820,860 B2 | 11/2004 | Gordon | |
| 7,058,488 B2 * | 6/2006 | Kemp et al. | 701/33 |
| 2003/0154054 A1 | 8/2003 | Charette et al. | |
| 2004/0003655 A1 | 1/2004 | Kemp et al. | |

FOREIGN PATENT DOCUMENTS

| | | |
|---|---|---|
| DE | 4323817 | 1/1994 |
| EP | 0299217 | 1/1998 |

(Continued)

OTHER PUBLICATIONS http://www.calinear.com/app-seat.htm, California Linear Devices, Inc., Seat Tester, Downloaded Jul. 22, 2005.

(Continued)

*Primary Examiner*—Eric S McCall
(74) *Attorney, Agent, or Firm*—Fish & Richardson P.C.

(57) ABSTRACT

A vehicle testing system includes a wheel plate constructed and arranged to support a vehicle wheel. A linear electromagnetic actuator has a moving magnet mechanically coupled to the wheel plate constructed and arranged to impart a controlled substantially vertical force to the wheel plate. A spring may be mechanically coupled to the wheel plate to support at least a portion of a static mass of the vehicle.

4 Claims, 5 Drawing Sheets

FOREIGN PATENT DOCUMENTS

| | | |
|---|---|---|
| EP | 1 326 066 | 7/2003 |
| SE | 1414943 | 1/1974 |
| WO | WO 93/01483 | 1/1993 |
| WO | WO 98/06590 | 2/1998 |
| WO | WO 02/01177 A1 | 1/2002 |

OTHER PUBLICATIONS http://www.lds-group.com/docs/display_group.php?group_id=118&application_id=1, Vibration Test Systems—Electrodynamic Shaker Systems, Downloaded Jul. 22, 2005.

http://www.teamcorporation.com/4poster.php, Team Corporation, Vibration Testing Solutions, Downloaded Jul. 22, 2005.

http://www.teamcorporation.com/vertical.php, Team Corporation, Vertical Vibration Systems, Downloaded Jul. 22, 2005.

http://www.teamcorporation.com/mantis.php, Team Corporation, Mantis™ Vibration Test System, Downloaded Jul. 22, 2005.

Birdsong, Charles, Ph.D., An Integrated Measurement to Road Vibration Simulation System, Dactron, Inc., Oct. 15, 2001.

www.bksv.com, Vibration Test and Control, pp. 54-55, Downloaded Jul. 22, 2005.

International Search Report and Wirtten Opinion in Application PCT/US2006/033102, dated Jan. 12, 2007 33 pgs.

* cited by examiner

VEHICLE TESTING APPARATUS FOR APPLYING VERTICAL FORCE TO A WHEEL

This application claims priority under 35 U.S.C. §119(e) to patent application No. 60/711,882, entitled VEHICLE TESTING, filed on Aug. 26, 2005.

The present invention relates in general to vehicle testing and more particularly concerns vehicle testing with a linear electromagnetic actuator.

BACKGROUND OF THE INVENTION

Vehicle road simulators or so-called four posters are used for chassis and component durability testing, evaluation of vehicle squeak and rattle characteristics, and performance testing of suspension systems.

SUMMARY OF THE INVENTION

It is an important object of the invention to provide improved vehicle testing with four post supports.

In general, in an aspect, an apparatus for testing a vehicle includes a frame separate from the vehicle to support at least a portion of a wheel of the vehicle, and a linear electromagnetic actuator at least partially contained within the frame, the linear electromagnetic actuator comprising a movable magnet and constructed and arranged to impart a controlled substantially vertical force to a vehicle wheel.

Implementations may include one or more of the following features. A wheel plate is coupled to the linear electromagnetic actuator and constructed and arranged to support the vehicle wheel and transmit vertical forces from the moveable magnet to the supported vehicle wheel. The wheel plate includes a butter plate. A controller is coupled to the linear electromagnetic actuator and constructed and arranged to furnish signals to the linear electromagnetic actuator to control the moveable magnet motion. The bandwidth of the linear electromagnetic actuator is sufficient to embrace a wheel hop frequency of the wheel. A spring is constructed and arranged to support at least a portion of the static mass of at least one vehicle wheel and the vehicle. The spring is from the group comprising a coil spring, a torsional spring, a leaf spring, an air spring and an air bag. There are a plurality of the apparatus constructed and arranged to impart controlled vertical forces on a corresponding plurality of supported vehicle wheels. There are a plurality of air springs constructed and arranged to provide leveling of a supported vehicle. A vehicle is tested with the apparatus by positioning a vehicle wheel mechanically coupled to the moving magnet, and applying controlled electrical energy to the linear electromagnetic actuator to impart controlled motion to the vehicle wheel. The spring includes an air spring which surrounds the linear electromagnetic actuator. The linear electromagnetic actuator includes bellows. The apparatus comprises a portable one poster vehicle testing apparatus. The signals are generated in response to a program representative of road simulation. The signals are generated in response to a program and are representative of vehicle suspension testing. The signals are generated in response to a program and are representative of driving conditions. The signals being generated in response to a program and are representative of frequency sweeps.

According to the method of the invention, position a wheel of the vehicle on the actuator assembly, support the mass of at least a portion of the wheel and vehicle with a static support, and energize the armature of the actuator assembly with the controller to induce controlled vehicle motion to the supported wheel. The method may be applied to all the wheels of the vehicle.

Other features, objects and advantages of the invention will become apparent from the following description when read in connection with the accompanying drawing in which:

DETAILED DESCRIPTION

Figure 1:
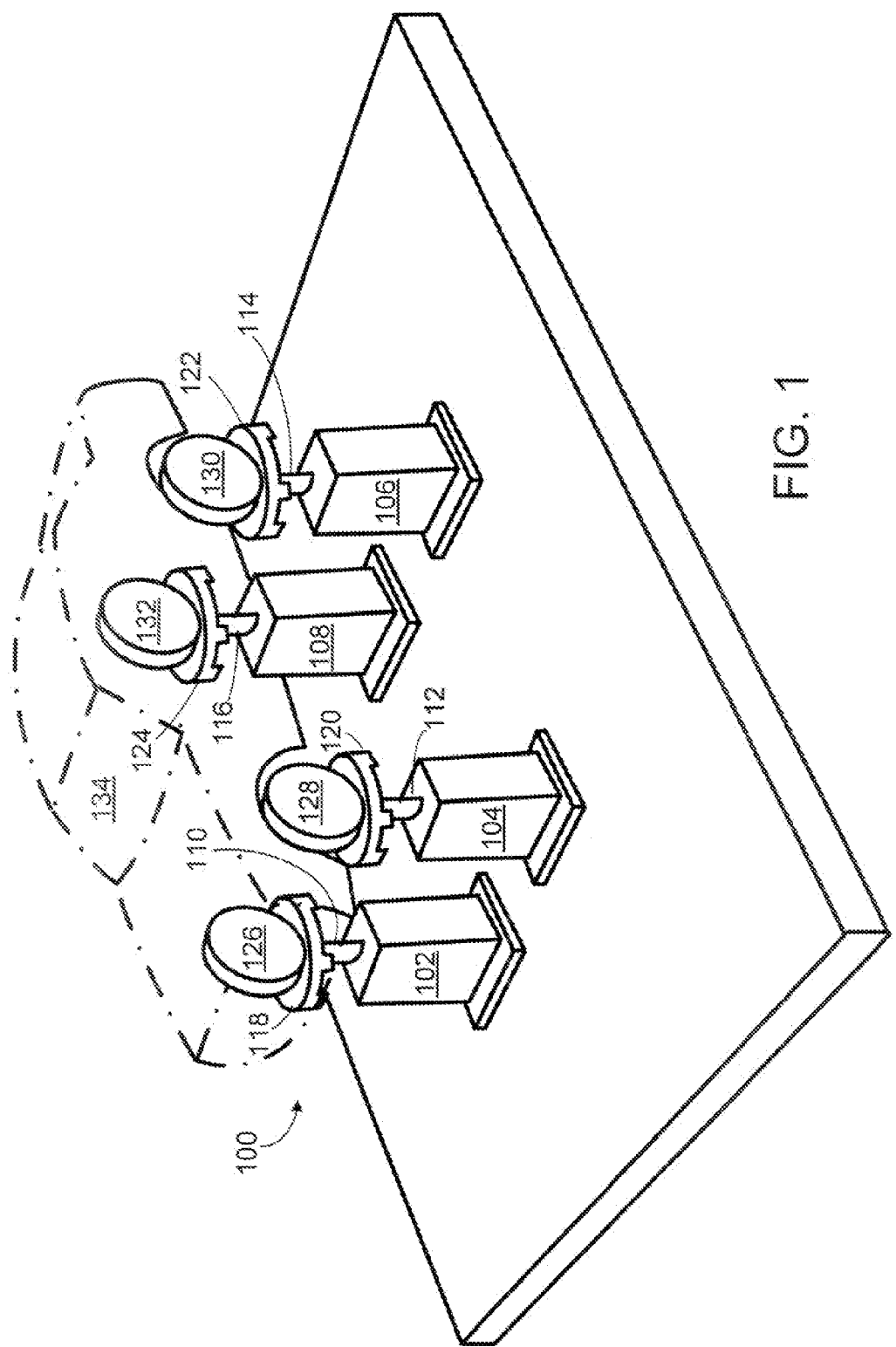
FIG. 1 is a perspective view of a four poster vehicle testing system according to the invention.

FIG. 1 is a perspective view of a four poster vehicle testing system 100 according to the invention. The four poster vehicle testing system 100 includes four individual actuator assemblies 102, 104, 106 and 108. Each of the actuator assemblies 102, 104, 106 and 108 includes a linear electromagnetic actuator having a moving magnet motor (not shown). An example of a linear electromagnetic actuator is described in U.S. Pat. No. 4,981,309, entitled "Linear Transducing Along a Path" incorporated herein by reference. Another example of a linear electromagnetic actuator is described in U.S. Pat. No. 5,701,039, entitled "Electromechanical Transducing" incorporated herein by reference.

The linear electromagnetic actuators include armatures 110, 112, 114 and 116. The armatures 110, 112, 114 and 116 include wheel plates 118, 120, 122 and 124. The wheel plates 118, 120, 122 and 124 can be configured as butter plates. A butter plate generally includes bearings that permit the butter plate to slide laterally relative to the armature to which it is attached. Each wheel plate 118, 120, 122 and 124 can include a clamp or strap that secures a wheel to the wheel plate 118, 120, 122 and 124. Other wheel clamping techniques can also be used.

Each of the wheel plates 118, 120, 122 and 124 is positioned under a wheel 126, 128, 130 and 132 of a vehicle 134. The actuator assemblies 102, 104, 106 and 108 of the four poster vehicle testing system 100 apply forces to the wheels 126, 128, 130 and 132. Each wheel may include a tire, a hub, a rim, a control arm or an axle. In some embodiments, each wheel plate 118, 120, 122 and 124 may be removed and the armatures 110, 112, 114 and 116 mechanically coupled to other components of the vehicle suspension. For example, the armatures 110, 112, 114 and 116 can be mechanically coupled to an "A" arm.

The actuator assemblies 102, 104, 106 and 108 are oriented to apply a substantially vertical force to the wheels 126, 128, 130 and 132. A controller (not shown) transmits force commands to the individual linear electromagnetic actuators. For example, the force commands can control the displacement, velocity, and/or acceleration of the linear electromagnetic actuators.

A spring (not shown) associated with each of the actuator assemblies 102, 104, 106 and 108 can be used to support at least a portion of the static mass of the vehicle 134. The spring can be a coil spring, a leaf spring, a torsional spring, or an air spring, for example. The air spring is sometimes referred to as an airbag. Air springs associated with each of the actuator assemblies 102, 104, 106 and 108 at each of the corners of the vehicle 134 can provide vehicle load leveling. In one embodiment, load leveling can be achieved by using one or more tilt sensors on the vehicle 134. The tilt sensors can measure degrees of levelness of the chassis in multiple dimensions. In one embodiment, the load leveling is achieved through the use of position sensors that measure the positions of the armatures 110, 112, 114 and 116 of each actuator assembly 102, 104, 106 relative to neutral positions of each armature 110, 112, 114 and 116.

In operation, the vehicle 124 is situated such that each of the wheels 126, 128, 130 and 132 is positioned on wheel plates 118, 120, 122 and 124, respectively. The vehicle testing system 100 can include ramps (not shown) which are used to maneuver the vehicle 134 into position. In one embodiment, the wheel plates 118, 120, 122 and 124 are substantially flush with a driving surface and the vehicle is simply maneuvered over the wheel plates 118, 120, 122 and 124. In another embodiment, a vehicle lift can be placed under the frame of the vehicle 134 to lift the vehicle 134 to an appropriate height. One of the actuator assemblies 102, 104, 106 and 108 can then be positioned under each of the wheels 126, 128, 130 and 132 of the vehicle 134. The actuator assemblies 102, 104, 106 and 108 can be movable to accommodate vehicles having wheel bases of different dimensions.

Once the vehicle 134 is properly positioned, the vehicle testing system 100 can be activated. Various tests and/or demonstrations can be automatically performed using the vehicle testing system 100. For example, the vehicle testing system 100 can be used to test and/or demonstrate vehicle suspensions.

In one embodiment, a single actuator assembly 102 can be used under one wheel 126 of the vehicle 134 to exercise the suspension components associated with that wheel 126. A one poster having a single actuator assembly 102 according to the invention can be constructed to be relatively small, light weight, and require a relatively small amount of power and a small amount of space to operate. Thus, the one poster can be designed to be portable and can be used in motor vehicle service stations or other facilities to test vehicle suspension components. For example, a vehicle shock absorber under test can be stimulated using the one poster. The test can indicate whether or not the shock absorber meets the manufacturer's specification and to what degree. A service manager can then recommend whether or when the component should be replaced. Other suspension components can also be tested, such as struts, control arms, bushings, etc.

In one embodiment, the one poster can be used under one wheel of the vehicle and then moved to another wheel of the vehicle. The wheels not be exercised by the one poster can be supported with jack stands having wheel plates. The jack stands can include airbags, hydraulics, or mechanical systems to adjust height. The wheel plates can include clamps that secure the wheels to the wheel plates.

Figure 2:
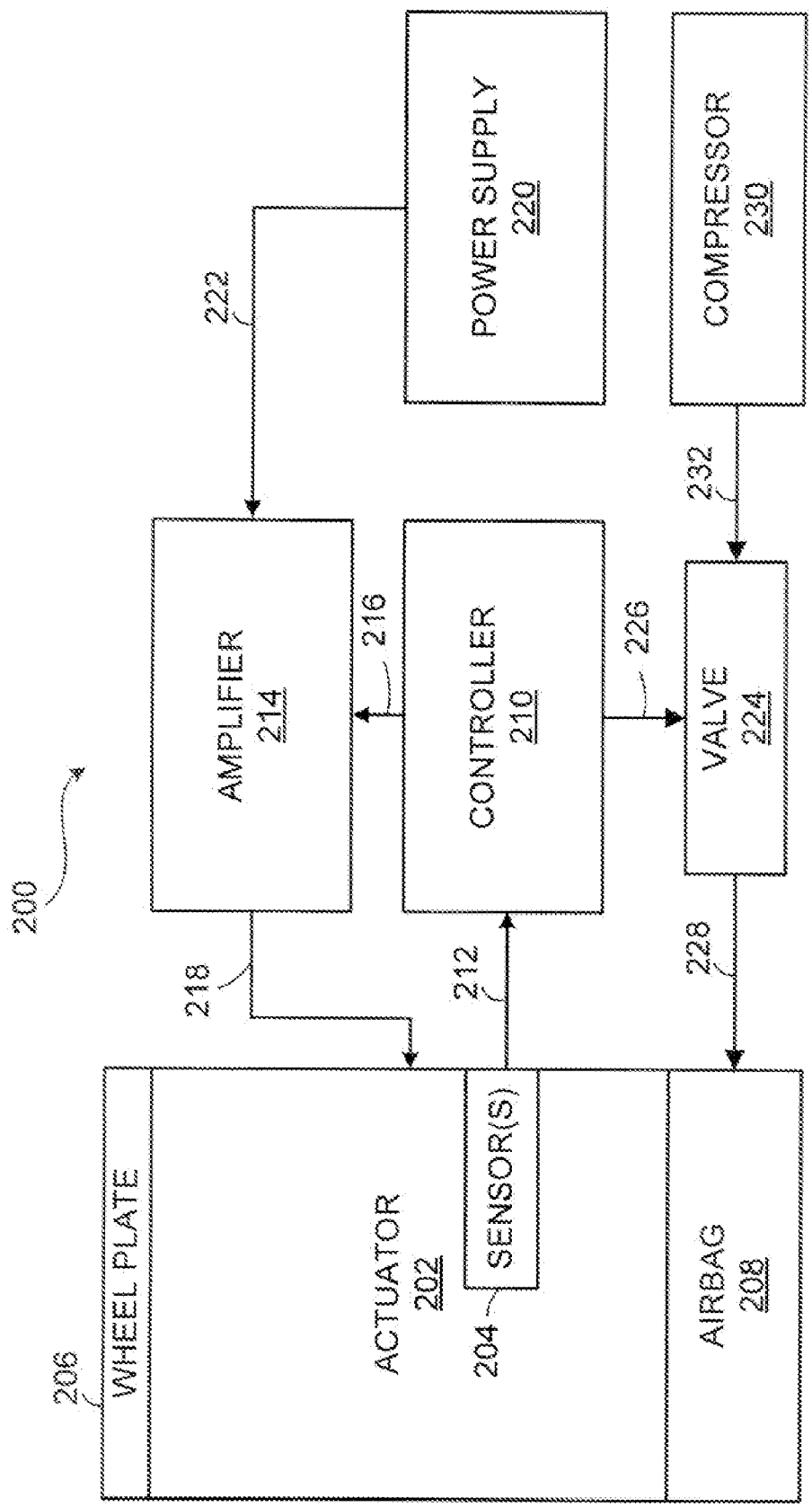
FIG. 2 is a block diagram of a one poster vehicle testing system according to the invention.

FIG. 2 is a block diagram of a one poster vehicle testing system 200 according to the invention. Although a one poster model is described, the embodiments of the invention can be applied to a four poster vehicle testing system 100, such as is described with reference to FIG. 1. The one poster vehicle testing system 200 is also referred to as a vehicle test stand. Thus, a four poster requires four vehicle test stands. The one poster vehicle testing system 200 includes an actuator 202. The actuator 202 is a moving magnet type linear electromagnetic actuator. The actuator 202 can be a high frequency actuator capable of exerting a controlled force at a frequency that is greater than a wheel hop frequency of a wheel of a vehicle. The wheel hop frequency is defined as a resonant frequency of the wheel. The wheel hop frequency is generally greater than about 9 Hz.

The actuator 202 can include one or more sensors 204. For example, the sensors 204 can include displacement sensors and/or accelerometers. The sensors 204 can measure the displacement of an armature (not shown) of the actuator 200 and/or the acceleration of the armature. In other embodiments, sensors can be used to measure the position, velocity, and/or acceleration of the armature. In some embodiments, combinations of sensors can be used.

The actuator 202 is coupled to a wheel plate 206. A tire of a wheel assembly is supported by the wheel plate 206. The wheel plate 206 can embody a butter plate. A butter plate is a device that allows a wheel of a vehicle to slide laterally.

In one embodiment, the wheel plate 206 is coupled to a spring through the armature. The spring is adapted to support at least a portion of the mass of the vehicle and/or at least a portion of the static mass of the vehicle component under test. In one configuration, the spring embodies an airbag 208. In other embodiments, the spring is directly coupled to the wheel plate 206.

The sensor 204 is coupled to a controller 210 through a signal transmission line 212. The controller 210 can include a computer, a microprocessor, or a digital signal processor (DSP), for example. The controller 210 receives sensor signals from the sensor(s) 204 and generates control signals in response to the sensor signals and/or in response to commands from a computer program. For example, a computer program can generate a road simulation test that simulates real road conditions. The controller 210 can receive data associated with the road simulation test as well as sensor signals to control the vehicle testing system 200. The computer program can also generate road profiles, different driving conditions, arbitrary test signals, sine waves, frequency sweeps and other waveforms.

In one embodiment, the controller 210 sends a control signal to an amplifier 214 through a signal transmission line 216. The amplifier 214 controls the motion of the actuator 202 through a power transmission line 218. A high voltage power supply 220 supplies power to the amplifier 214 through a power transmission line 222.

In one embodiment, the sensor(s) 204 send signals to the controller 210 or the amplifier 214 (assuming the amplifier contains the proper control circuitry) that indicates when the armature 306 is in a desired position. An optional feedback mechanism to accomplish this can be integrated into the controller 210 or the amplifier 214, for example. The neutral position can be a center position that allows the actuator 202 to translate up and down by the same distance relative to the center position.

The controller 210 can also control a valve 224 through a signal transmission line 226. The valve 224 is coupled to the airbag 208 through an air line 228. A compressor 230 is coupled to the valve 224 through an air line 232. The compressor 230 supplies pressurized air to the valve 224. The valve 224 is a two-way valve that can allow air into the airbag 314 and can allow air to escape from the airbag 314. Fluids or other gases in addition to air can also be used.

Figure 3:
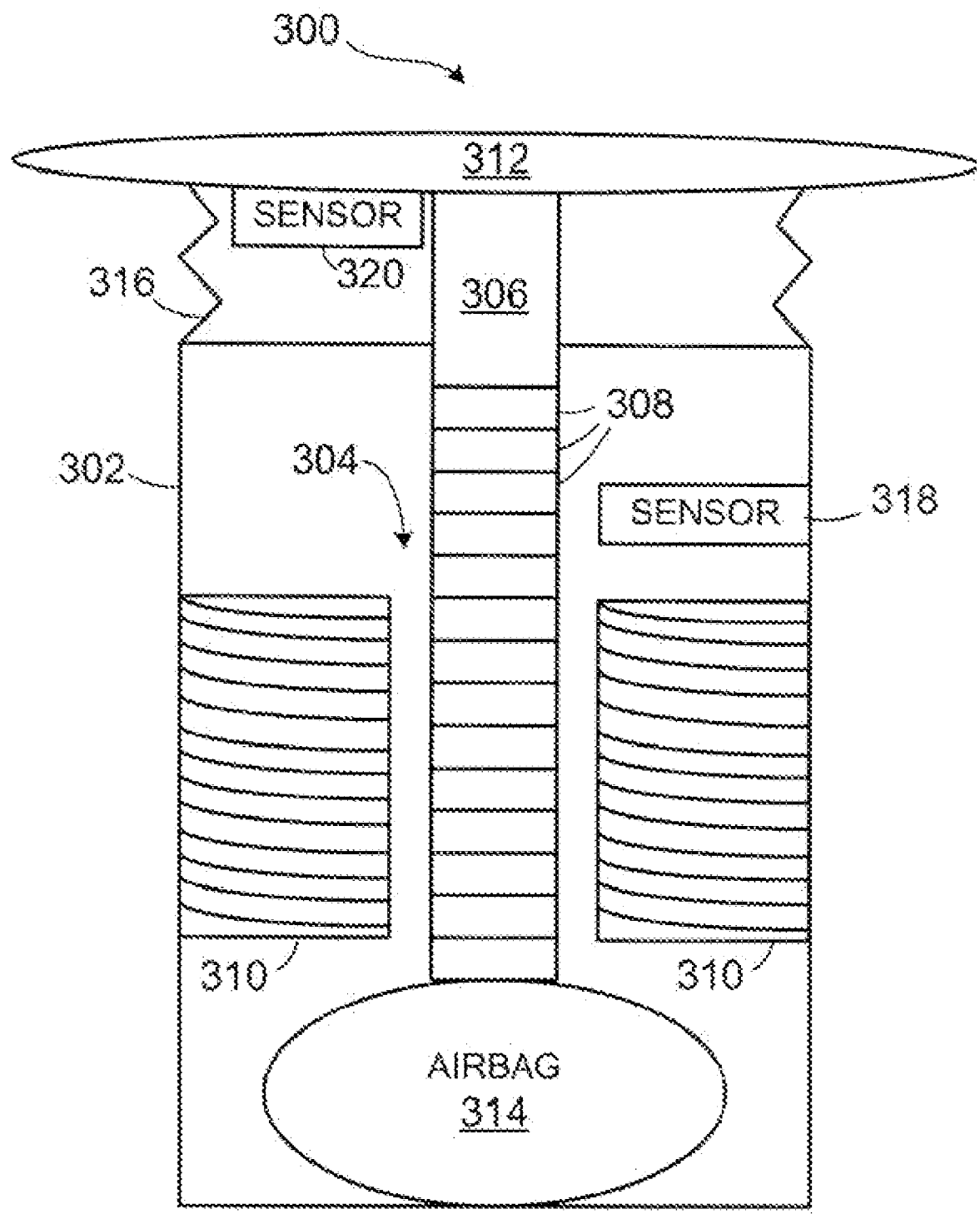
FIG. 3 is a sectional view of an actuator assembly according to one embodiment of the invention.

FIG. 3 is a sectional view of an actuator assembly 300 according to one embodiment of the invention. The actuator assembly 300 can be a component in a one poster or a component in a four poster, for example. The actuator assembly 300 includes a frame 302. A linear electromagnetic actuator 304 is at least partially contained within the frame 302. The linear electromagnetic actuator 304 includes a moving magnet armature 306 having one or more magnets 308. The magnets 308 can include rare earth-type magnets. The linear electromagnetic actuator 304 also includes coils 310. The linear electromagnetic actuator 304 can include a moving magnet motor having single or multiple phases.

The actuator assembly 300 can also include a wheel plate 312. The wheel plate 312 is coupled to the armature 306. The wheel plate 312 is constructed to support a wheel of a vehicle.

The actuator assembly 300 can also include an airbag 314. The airbag 314 is adapted to support at least a portion of the static mass of the wheel and/or the vehicle. The volume of the airbag 314 can be modified as desired. For example, an external bladder or tank (not shown) can be fluidly coupled to the airbag 314 to effectively increase the volume of air. The actuator assembly 300 can also include a bellows 316. The bellows 316 is designed to prevent foreign objects from entering and damaging the motor 304.

A first sensor 318 is coupled to the frame 302. The first sensor 318 can be a displacement sensor that measures the relative displacement of the armature 306. A second sensor 320 is coupled to a moving component of the actuator assembly 300. For example, the second sensor 320 can be coupled to the wheel plate 312 or the armature 306. The second sensor 320 can include a velocity sensor or an accelerometer.

The actuator assembly 300 can operate as follows. In one embodiment, in order to load the vehicle wheel onto the wheel plate 312, the armature 306 is mechanically secured or braced to a predetermined neutral position. A block positioned under the armature 306 can be used brace the armature 306. In another embodiment, a pin inserted through the armature 306 can be used to brace the armature 306. Other automatic or manual techniques to load the vehicle wheel onto the wheel plate 312 without requiring the linear electromagnetic actuator 304 to bear the static mass of the wheel and/or the vehicle can also be used.

In one embodiment, the linear electromagnetic actuator 304 can be used to bear the static mass of the wheel and/or the vehicle during loading. In this embodiment, the controller 210 instructs the valve 224 to inflate the airbag 314 to a predetermined pressure. The linear electromagnetic actuator 304 is energized and the controller 210 (FIG. 2) sends a command single to the amplifier 214 to bring the armature 306 to a neutral position within the motor coils 310. The sensor 204 sends a signal to the controller 210 or the amplifier 214 (assuming the amplifier contains the proper control circuitry) that indicates when the armature 306 is in the proper position. An optional feedback mechanism to accomplish this can be integrated into the controller 210 or the amplifier 214, for example. The neutral position can be a center position that allows the armature 306 to translate up and down by the same distance relative to the center position.

The linear electromagnetic actuator 304 applies a static force to the airbag 314 to precompress the airbag 314. As the wheel of the vehicle contacts the wheel plate 312, the controller 210 instructs the actuator 304 to controllably release the static force on the airbag 314. The controller 210 (via the valve 224) then adjusts the pressure in the airbag 314 to locate the armature 306 to a desired position. At least a portion of the static mass of the wheel and/or vehicle is then supported by the airbag 314. Other manual or automatic techniques can also be used to load a wheel of the vehicle onto the wheel plate 312.

A computer loads a program into the controller 210. In one embodiment, the controller 210 embodies the computer. For example, the program can be a road simulation program that is used to simulate substantially vertical forces imparted by a road surface to a wheel of the vehicle. The program inputs signals that are representative of the desired motion to the controller 210. The controller 210 transmits force commands to the amplifier 214, thereby directing the actuator 304 to move a predetermined direction with a predetermined velocity according to the desired motion. The sensors 318, 320 transmit sensor signals to the controller 210. The sensor signals can communicate the position of the armature 306 and the acceleration of the armature 306, for example. The controller 210 also controls the valve 224. The valve 224 can increase or decrease the pressure in the airbag 314 in response to commands from the controller 210.

Upon completion of the program, the controller 210 commands the armature 306 of the actuator 304 to be brought to a neutral center position. The airbag 314 is inflated so that the armature 306 can be mechanically secured or braced.

Figure 4:
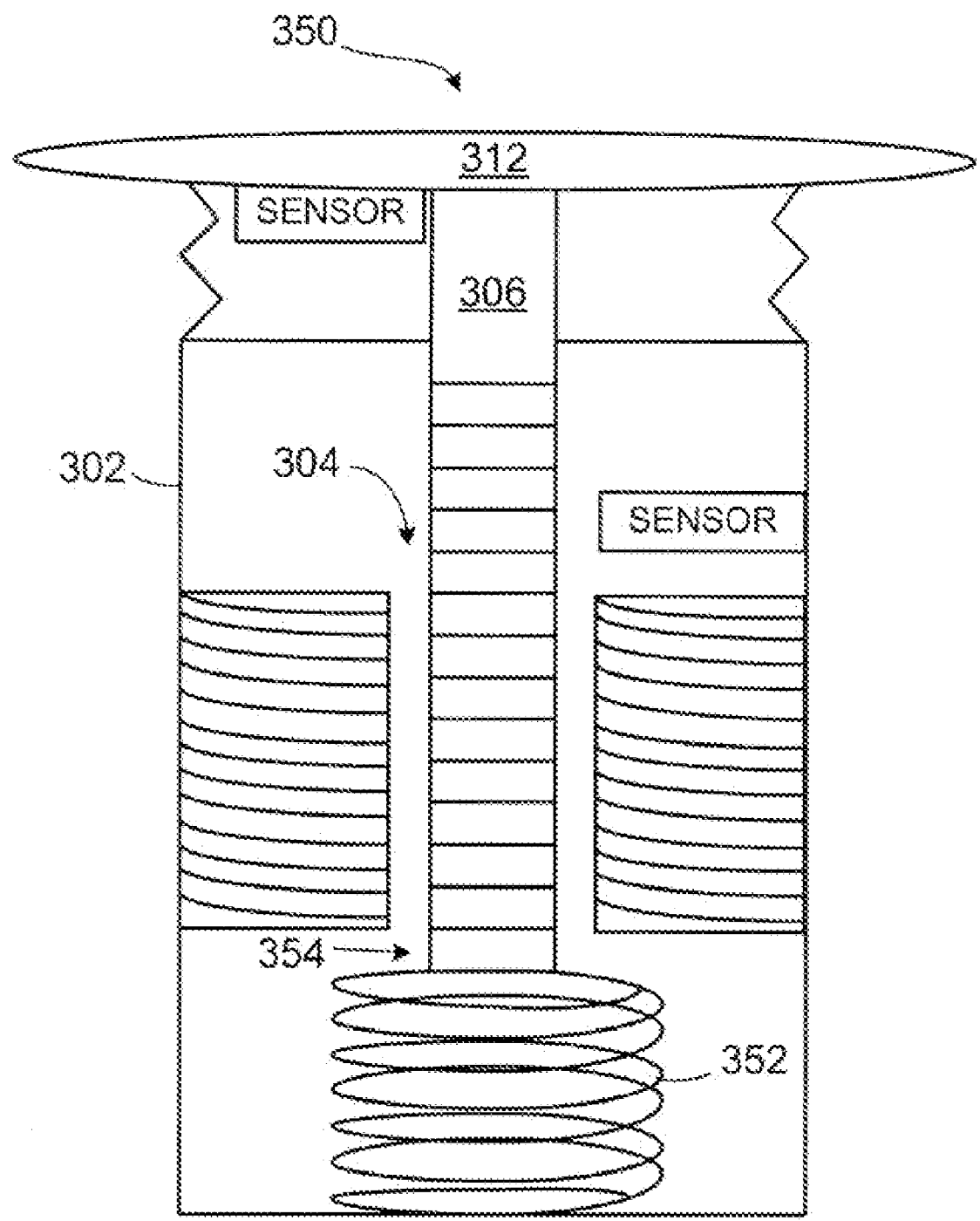
FIG. 4 is a sectional view of an actuator assembly according to another embodiment of the invention.

FIG. 4 is a sectional view of an actuator assembly 350 according to another embodiment of the invention. The actuator assembly 350 contains substantially similar components to the actuator assembly 300 of FIG. 3. However, the airbag 314 of FIG. 3 is replaced by a coil spring 352. The coil spring 352 is configured to support at least a portion of the mass of the vehicle and/or the wheel when a wheel of the vehicle is positioned on the wheel plate 312. In one embodiment, the coil spring 352 is a non-linear spring. For example, the coil spring 352 can be designed to include a spring constant that varies as the spring is compressed.

Other springs having different configurations can also be used. For example, a torsional spring or a leaf spring can be used. In one embodiment (not shown), one end 354 of the actuator 306 is attached to rubberized cords that are configured to support at least a portion of the mass of the vehicle and/or the wheel.

Figure 5:
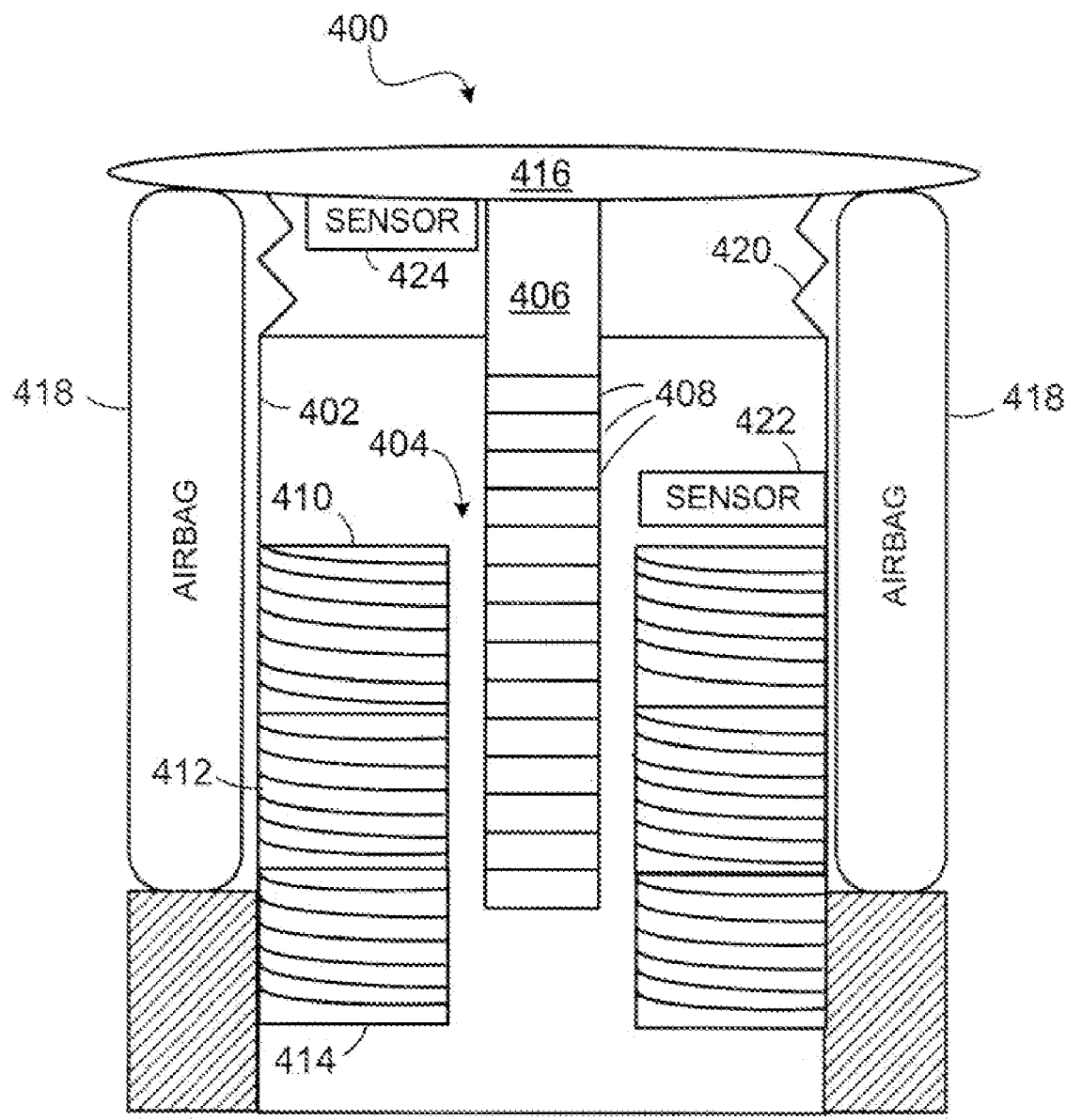
FIG. 5 is a sectional view of an actuator assembly according to yet another embodiment of the invention.

FIG. 5 is a sectional view of an actuator assembly 400 according to yet another embodiment of the invention. The actuator assembly 400 can be a component in a one poster or a component in a four poster, for example. The actuator assembly 400 includes a frame 402. A linear electromagnetic actuator 404 is at least partially contained within the frame 402. The linear electromagnetic actuator 404 includes a moving magnet armature 406. The moving magnet armature 406 includes a plurality of magnets 408. The magnets 408 can include rare earth-type magnets. The linear electromagnetic actuator 404 also includes a plurality of coils 410, 412, 414. The coils 410, 412, 414 can be used to create a multiple phase linear motor. The embodiments described with reference to FIG. 3 and FIG. 4 can also include a moving magnet motor having multiple coils.

The actuator assembly 400 can also include a wheel plate 416. The wheel plate 416 is coupled to the armature 406. The wheel plate 416 is constructed to support a tire associated with a wheel of a vehicle. As previously described, the wheel plate 416 can embody a butter plate.

The actuator assembly 400 can also include one or more airbags 418. The one or more airbags 418 can be located externally to the frame 402. For example, the airbag 418 can at least partially surround the frame 402. The airbag 418 is adapted to support at least a portion of the static mass of the wheel and/or the vehicle. The volume of the airbag 418 can be varied. The actuator assembly 400 can also include an optional bellows 420. In one embodiment, the airbag 418 can be designed to surround the actuator 404, thereby obviating the need for the bellows 420. In this configuration, the airbag 418 prevents foreign objects from entering and damaging the motor 304.

A first sensor 422 is coupled to the frame 402. The first sensor 422 can be a displacement sensor that measures the relative displacement of the armature 406. A second sensor 424 is coupled to a moving component of the actuator assembly 400. For example, the second sensor 424 can be coupled to the wheel plate 416 or the armature 406. The second sensor 424 can include a velocity sensor or an accelerometer.

The actuator assembly 400 can operate in a manner that is similar to the operation of the actuator assembly 300 of FIG. 3.

There has been described novel apparatus and techniques for vehicle component testing, especially vehicle suspension component testing. It is evident that those skilled in the art may now make numerous modifications of and departures from the specific apparatus and techniques described herein without departing from the inventive concepts. Consequently, the invention is to be construed as embracing each and every feature and novel combination of features present in or possessed by the apparatus and techniques herein disclosed and limited solely by the spirit and scope of the appended claims.

What is claimed is:

1. A system for testing a vehicle comprising:
   a plurality of apparatus, each of the plurality of apparatus comprising:
      a frame separate from the vehicle and configured to support at least a portion of a wheel of the vehicle; and
      a linear electromagnetic actuator at least partially contained within the frame, the linear electromagnetic actuator comprising a movable magnet and being constructed and arranged to impart a controlled substantially vertical force to a vehicle wheel;
   wherein each of the plurality of apparatus is arranged to independently impart controlled substantially vertical force on a corresponding one of a plurality of supported vehicle wheels; and
   a plurality of air springs constructed and arranged to provide leveling of a supported vehicle.

2. An apparatus for testing a vehicle comprising:
   a frame separate from the vehicle and configured to support at least a portion of a wheel of the vehicle;
   a linear electromagnetic actuator at least partially contained within the frame, the linear electromagnetic actuator comprising a movable magnet and being constructed and arranged to impart a controlled substantially vertical force to a vehicle wheel; and
   a spring constructed and arranged to support at least a portion of a static mass of at least one vehicle wheel and the vehicle, wherein the spring comprises an air spring which surrounds the linear electromagnetic actuator.

3. An apparatus for testing a vehicle comprising:
   a frame separate from the vehicle and configured to support at least a portion of a wheel of the vehicle; and
   a linear electromagnetic actuator at least partially contained within the frame, the linear electromagnetic actuator comprising a bellows and a movable magnet, the linear electromagnetic actuator being constructed and arranged to impart a controlled substantially vertical force to a vehicle wheel.

4. A portable one poster vehicle testing apparatus comprising:
   a frame separate from the vehicle and configured to support at least a portion of one wheel of the vehicle; and
   a linear electromagnetic actuator at least partially contained within the frame, the linear electromagnetic actuator comprising a movable magnet and being constructed and arranged to impart a controlled substantially vertical force to the one vehicle wheel.

* * * * *